(12) United States Patent
DiMauro et al.

(10) Patent No.: US 7,351,253 B2
(45) Date of Patent: Apr. 1, 2008

(54) INTRANASAL RED LIGHT PROBE FOR TREATING ALZHEIMER'S DISEASE

(75) Inventors: Thomas M. DiMauro, Southboro, MA (US); Mohamed Attawia, Canton, MA (US); Sean Lilienfeld, Sharon, MA (US); Chantal Holy, Raynham, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 71 days.

(21) Appl. No.: 11/154,754

(22) Filed: Jun. 16, 2005

(65) Prior Publication Data
US 2006/0287695 A1 Dec. 21, 2006

(51) Int. Cl.
*A61N 5/06* (2006.01)
(52) U.S. Cl. .......................... 607/88; 128/898
(58) Field of Classification Search ................ 128/898; 607/88–94
See application file for complete search history.

(56) References Cited

U.S. PATENT DOCUMENTS

| 2,227,422 | A | * | 1/1941 | Boerstler | 607/93 |
| 5,683,436 | A | * | 11/1997 | Mendes et al. | 607/88 |
| 6,537,304 | B1 | | 3/2003 | Oron | |
| 6,551,346 | B2 | * | 4/2003 | Crossley | 607/88 |
| 2002/0029071 | A1 | * | 3/2002 | Whitehurst | 607/88 |
| 2003/0097122 | A1 | | 5/2003 | Ganz | |
| 2004/0030368 | A1 | | 2/2004 | Kemeny | |
| 2004/0116985 | A1 | * | 6/2004 | Black | 607/89 |
| 2004/0127961 | A1 | * | 7/2004 | Whitehurst | 607/88 |
| 2005/0107851 | A1 | | 5/2005 | Taboada | |
| 2005/0107853 | A1 | * | 5/2005 | Krespi et al. | 607/89 |

FOREIGN PATENT DOCUMENTS

| RU | 2200041 | 3/2003 |
| RU | 2200041 | 1/2004 |
| RU | 2222362 | 1/2004 |

OTHER PUBLICATIONS

Yaroslavsky, Optical Properties of Selected Native and Coagulated human Brain Tissue In Vitro In The Visible and Near Infrared Spectral Range, Phys. Med. Biol., 2002, pp. 2059-2073, vol. 47.
Wong-Riley, Light-emitting diode treatment reverses the effect of TTX on cytochrome osidase in neurons, Neuroreport, Oct. 8, 2001, pp. 3033-3037, vol. 12(14).
Yamamoto, Involvement of the olfactory system in learning and memory: a close correlation between the olfactory deficit and the course of Alzheimer's disease?. Yakubutsu Seishin Kodo, 1991, pp. 223-235, vol. 11(4).
Yamamoto, Characteristics of memory dysfunction in olfactory bulbectomized rats and the effects of cholinergic drugs. Behav Brain Res, Feb. 1997, pp. 57-62, vol. 83(1-2).
Volotovskaia, Antioxidant action and therapeutic efficacy of laser irradiation blood in patients with ischemic heart disease, Vopr Kurortol Lech Fiz Kult, May-Jun. 2003, pp. 22-25, vol. 3.

(Continued)

Primary Examiner—Henry M Johnson, III

(57) ABSTRACT

A method of treating Alzheimer's Disease in which intranasal red light devices are used to shine red light upon the brain structures.

11 Claims, 16 Drawing Sheets

OTHER PUBLICATIONS

Vladimirov, Molecular and cellular mechanisms of the low intensity laser radiation effect, Biofizika, Mar.-Apr. 2004, pp. 339-350, vol. 49(2).

Sohranji, Local and cortical effects of olfactory bulb lesions on trophic support and cholingeric function and their modulation by estrogen, J Neurobiol, Nov. 2000, pp. 61-74, vol. 45(2).

Tsuboi, Tau pathology in the olfactory bulb correlates with Braak stage, Lewy body pathology and apolipoprotein epsilon4, Neuropathol Appl Neurobiol., Oct. 2003, pp. 503-510, (5).

Powers, Light dosimetry in brain tissue: an in vivo model applicable to photodynamic therapy, Lasers Surg Med., 1986, pp. 318-322, vol. 6(3).

Qiu, Interleukin-6, beta-amyloid peptide and NMDA interactions in rat cortical neurons, J Neuroimmunol, 2003, pp. 51-57, vol. 139(1-2).

Romm, Action of laser radiation on the peroxide chemiluminescence of wound exudate, Biull Eksp Biol Med., Oct. 1986, pp. 426-428, vol. 102(10).

Mann, Alzheimer's disease: an olfactory connection?, Mech Ageing Dev., Jan. 1099, pp. 1-15, vol. 42(1).

Hozumi, Characteristics of changes in cholinergic function and impairment of learning and memory-related behavior induced by olfactory bulbectomy, Behav Brain Res., Jan. 2003,pp. 9-15, vol. 138(1).

Huell, Interleukin-6 is present in early stages of plaque formation and is restricted to the brains of Alzheimer's disease patients, Acta Neuropathol (Berl), 1995, pp. 544-551, vol. 89(6).

Iakymenko, Regulatroy role of low-intensity laser radiation on the status of antioxidant system, Ukr. Biokhim Zh., Jan.-Feb. 2001, pp. 16-23, vol. 73(1).

Ji, Interstitial photoradiation injury of normal brain, Lasers Surg Med, 1992, pp. 425-431, vol. 12(4).

Kamanli, Plasma lipid peroxidation and antioxidant levels in patients with rheumatoid arthritis, Cell Biochem Funct., Jan.-Feb. 2003, pp. 53-57, vol. 22(1).

Klebanov, Effect of low intensity laser light in the red range on macrophages superoxide dismutase activity, Biofizika, May-Jun. 2003, pp. 462-473, vol. 48(3).

Konchugova, Immunodepressive effect of transcerebral lasers, Biull Eksp Biol Med., Apr. 1993, pp. 391-393, vol. 115 (4).

Kovacs, beta-amyloid deposition and neurofibrillary tangle formation in the olfactory bulb in ageing and Alzheimer's disease, Neuropathol Appl Neurobiol., Dec. 1999, pp. 481-491, vol. 25(6).

Kovacs, Olfactory centres in Alzheimer's disease: olfactory bulb is involved in early Braak's stages, Neuroreport., Feb. 2001, pp. 285-288, vol. 12(2).

Chen, Effects of light beam size on fluence distribution and depth of necrosis in superficially applied photodynamic therapy of normal rat brain, Photochem Photobiol., Sep. 1992, pp. 379-384, vol. 56(3).

Cottrell, Mitochondrial enzyme-deficient hippocompal neurons and choroidal cells in AD., Neurology, Jul. 2001, pp. 260-264, vol. 57(2).

Cottrell, The role of cytochrome c oxidase deficient hippocampal neurons in Alzheimer's disease, Neuropathol Appl Neurobiol., Oct. 2002, pp. 390-396, vol. 28(5).

Davies, Axonal loss from the olfactory tracts in Alzheimer's disease, Neurobiol Aging., Jul.-Aug. 1993, pp. 353-357, vol. 14(4).

Del Bo, Reciprocal control of inflammatory cytokines, IL-1 and IL-6, and beta-amyloid production in cultures, Neurosci Lett., Mar. 1995, pp. 70-74, vol. 188(1).

Elias, Hyperthermia from interstitial laser irradiation in normal rat brain, Lasers Surg Med., 1987, pp. 370-375, vol. 7(4).

Giuliani, Very low level laser therapy attenuates edema and pain in experimental models, Int J Tissue React., 2004, pp. 29-37, vol. 26(1-2).

Gorbatenkova, Reactivation of superoxide dismutase by the helium-neon laser irradiation, Biofizika, Jul.-Aug. 1988, pp. 717-719, vol. 33(4).

Gorbatenkova, The red light of the helium-neon laser reactivates superoxide dismutase, Biull Eksp Biol Med., Mar. 1989, pp. 302-305, vol. 107(3).

Haas, Inducible nitric oxide synthase and argininosuccinate synthetase: co-induction in brain tissue of patients with Alzheimer's dementia and following stimulation with beta-amyloid 1-42 in vitro, Neurosci Lett., Apr. 5, 2002, pp. 121-125, vol. 322(2).

Hallam, An investigation of the effect of tacrine and physostigmine on spatial working memory deficits in the olfactory bulbectomised rat, Behav Brain Res., Aug. 31, 2004, pp. 481-486, vol. 153(2).

Wollman, Low power laser irradiation enhances migration and neurite sprouting of cultured rat embryonal brain cells, Neurological Research, Oct. 1996, pp. 467-470, vol. 18.

Snyder, Quantitation of Calcitonin Gene-Related Peptide mRNA and Neuronal Cell Death in Facial Motor Nuclei Following Axotomy and 633 nm Low Power Laser Treatment, Lasers in Surgery and Medicine, 2002, pp. 216-222, vol. 31.

Vladimirov, Photobiological Principles of Therapeutic Applications of Laser Radiation, Biochemistry, 2004, pp. 81-90, vol. 69(1).

Vladimirov, Photoreactivation of Superoxide Dismutase by Intensive Red (Laser) Light, Free Radical Biology & Medicine, 1988, pp. 281-286, vol. 5.

Schindl, Low-Intensity Laser Therapy: A Review, Journal of Investigative Medicine, Sep. 2000, pp. 312-326, vol. 48(5).

Mochizuki-Oda, Effects of near-infra-red laser irradiation on adenosine triphosphate and adenosine diphosphate contents of rat brain tissue, Neuroscience Letters, 2002, pp. 207-210, vol. 323.

Leung, Treatment of Experimentally Induced Transient Cerebral Ischemia With Low Energy Laser Inhibits Nitric Oxide Synthase Activity and Up-Regulates the Expression of Transforming Growth Factor-Beta 1, Lasers in Surgery and Medicine, 2002, pp. 283-288, vol. 31.

Hebeda, Light Propagation in the Brain Depends on Nerve Fiber Orientation Experimental Study, Neurosurgery, Oct. 1994, pp. 1992-1998, vol. 35(4).

Byrnes, Light Promotes Regeneration and Functional Recovery and Alters the Immune Response After Spinal Cord Injury, Lasers in Surgery and Medicine, 2005, pp. 1-15, vol. 9999.

Anders, Phototherapy promotes regeneration and functional recovery of injured peripheral nerve, Neurological Research, Mar. 2004, pp. 233-239, vol. 26.

Aliev, Atherosclerotic lesions and mitochondria DNA deletions in brain microvessels as a central target for the development of human AD and AD-like pathology in aged transgenic mice, Ann N Y Acad Sci., Nov. 2002, pp. 45-64, vol. 977.

Cho, Effect of low-level laser therapy on osteoarthroplasty in rabbut, In Vivo, Sep.-Oct. 2004, pp/ 585-591, vol. 18(5).

Balaban, He-Ne laser irradiation of single identified neurons, Lasers Surg Med, 1992, pp 329-337, vol. 12(3).

Aleksandrova, Increased level of beta-amyloid in the brain of bulbectomized mice, Feb. 2004, pp. 176-180, vol. 69 (2).

Anders, Low power laser irradiation alters the rate of regeneration of the rat facial nerve, Lasers Surg Med., 1993, pp. 72-82, vol. 13(1).

Wollman, In vitro cellular processes sprouting in cortex microexplants of adult rat brains induced by low power laser irradiation, Neurologic Research, Jul. 1998, pp. 470-472, vol. 20.

Dugan, Fullerene-based antioxidants and neurodegenerative disorders, Parkin. Relat. Disord., 1002, Jul., pp. 243-246, vol. 7 (3).

Ebadi, Peroxynitrite and mitochondrial dysfunction in the pathogenesis of Parkinson's disease, Antioxidants & Redox Signaling, 2003, pp. 319-335, vol. 5(3).

Gonzalez, Protection against MPP+ neurotoxicity in cerebellar granule cells by antioxidants, Cell Biology Int'l, (2004) pp. 373-380, vol. 28.

Itoh, Defects of Cytochrome c Oxidase in the Substantia Nigra of Parkinson's Disease: An Immunohistochemical and Morphometric Study., Mov. Disord., Jan. 1997, pp. 9-16, vol. 12(1).

Karu, Suppression of Human Blood Chemiluminescence By Diode Laser Irradiation at Wavelengths 660, 820, 880 or 950 nm., Laser Ther. 1993, pp. 103-109, vol. 5.

Nakao, Overexpressing Cu/Zn superoxide dismutase enhances survival of transplanted neurons in a rat model of Parkinson's disease, Nat. Med. Mar. 1995, pp. 226-231 vol. (3).

Ostrakhovich, Active forms of oxygen and nitrogen in blood cells of patients with rheumatoid arthritis: effect of laser therapy, Vestn Ross Akad Med Nauk. 2001, pp. 23-27, vol. 5.

Vitreshchak, Laser Modification of the Blood in Vitro and in Vivo in Patients with Parkinson's Disease Bull. Exp. Biol. Med. May 2003 430-432, vol. 135(5).

Walicke, Purification of a human red blood cell protein supporting the survival of cultured CNS neurons and its identification as catalase, J. Neuroscience, Apr. 1986, pp. 1114-1121, vol. 6(4).

Wong-Riley, Photobiomodulation directly benefits primary neurons functionally inactivated by toxins: role of cytochrome c oxidase, J. Biol. Chem. Feb. 11, 2005, pp. 4761-4771, 280(6), Epub Nov. 22, 2004.

ISR dated Jan. 5, 2007.

Neuman et al; "Narrow-band red light phototherapy in perennial allergic rhinitis and nasal polyposis".

Ann Allergy Asthma Immunology. Apr. 1997; 78 (4):399-406.

* cited by examiner

FIG. 5A
FIG. 5B
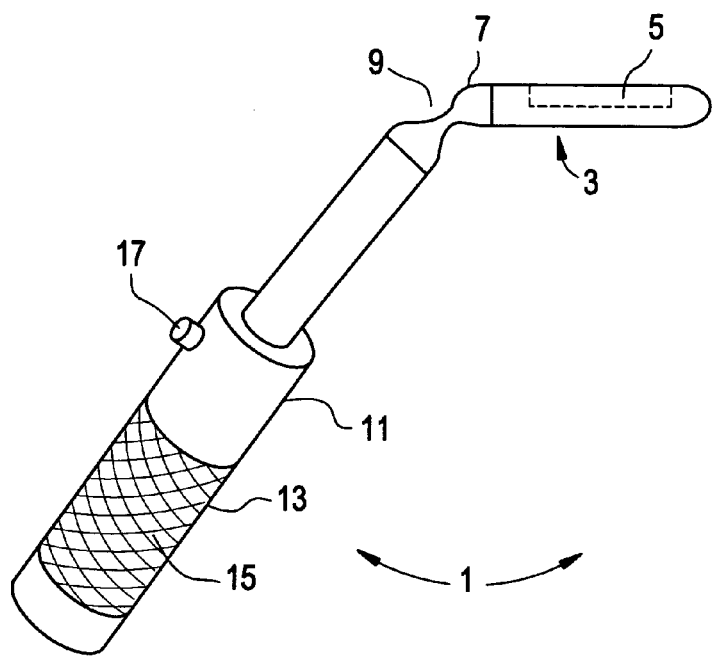
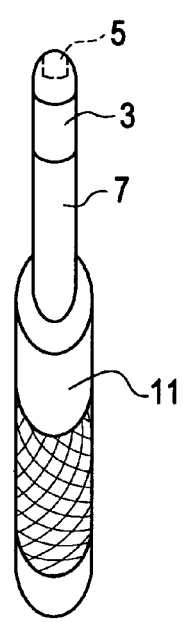

INTRANASAL RED LIGHT PROBE FOR TREATING ALZHEIMER'S DISEASE

BACKGROUND OF THE INVENTION

In Alzheimer's Disease (AD), the cleavage of beta amyloid protein precursor from the intracellular membrane often produces a protein AB-42 which is incompletely removed by normal clearance processes. Over time, this protein is deposited as a beta amyloid protein (Aβ) plaque within brain tissue, leading to the local destruction of neurons. The Aβ plaque deposition is also believed to provoke an inflammatory response by microglia and macrophages. These cells are believed to respond to the plaque deposition by releasing pro-inflammatory cytokines and reactive oxygen species (ROS). Although the inflammatory response may be provoked in an effort to clear the brain tissue of the detrimental plaque, it is now believed that this inflammation also injures local neuronal tissue, thereby exacerbating AD.

Now referring to FIG. 1, in most AD cases, the progression of AD begins in the hippocampus, wherein the patient suffers a loss of short term memory. From the hippocampus, the disease spreads to the amydgala, and then proceeds anteriorly to the prefrontal cortex. Since the prefrontal cortex controls problem-solving, a person suffering from AD begins to lose their ability to learn when the disease affects the prefrontal cortex. In general, impairment of the prefrontal cortex begins to appear a few years after loss of short-term memory.

The olfactory bulb (OB) is located just above the top of the nasal cavity and is intimately involved in the sense of smell. Olfactory nerve fibers located in the nasal cavity extend through the cribriform plate and enter the OB along its longitudinal axis. The OB projects through the lateral olfactory tracts to the olfactory tubercles, the pyriform cortex, the cortical amydgala nucleus and the ventrolateral entorhinal area.

There is substantial evidence that the OB is one of the first portions of the brain affected by AD. Davies, *Neurobiol. Aging,* 1993, July-August 14(4) 353-7. Investigators have found significant early tau-related pathology in the OB of AD patients. Tsuboi, *Neurpathol., Appl. Neurobiol.* 2003, October 29(5) 503-10. Increased numbers of neuritic plaques and neurofibrillary tangles on the OB have been demonstrated in AD patients. Yamamoto, *Yakunutsu Seishin Kodo,* August 11(4), 223-35.

In addition to its olfactory functions, the OB is particularly rich in acetylcholine and other neurotransmitters and delivers these neurotransmitters to other portions of the brain. Since the OB is well interconnected within the brain, destruction of the OB by AD may well lead to accelerated destruction of other portions of the AD brain. Some investigators have suggested that neural injury to the OB may result in collateral damage to other limbs of the cholinergic system. For example, it has been found that lesioning of the OB results in severely reduced expression of BDNF expression in an afferent structure, the hlDBB, and reduced choline uptake and ChAT activity locally and in the cingulated cortex. Sohrabji, *J. Neurobiol.,* 2000, Nov. 5, 45(2) 61-74. Some investigators have found that the most severely affected areas of the AD brain are interconnected with the central olfactory system in contrast to the relative sparing of the other sensory areas which lack olfactory connection. Kovacs, *Neurpathol., Appl. Neurobiol.,* 1999, December 25(6) 481-91.

Indeed, many investigators have reported that olfactory bulbectomy leads to severe impairment in memory or learning. Yamamoto, *Yakunutsu Seishin Kodo,* August 11(4), 223-35; Yamamoto, *Behav. Brain. Res.* 1997, February 83(1-2) 57-62; Hozumi, *Behav. Brain Res.* 2003, Jan. 6, 138(1) 9-15; and Hallam, *Behav. Brain Res.* 2004, Aug. 31, 153(2):481-6. Hallam, supra, and Hozumi, supra, have tied this collateral deficit to impairment of the cholinergic system. Other investigators have suggested that bulbectomy initiates in the brain a pathological process similar to human Alzheimer's Disease in location, biochemistry and behavioural manifestations. Aleksandrova, *Biochemistry (Mosc),* 2004, February 69(2) 176-180.

A minority of investigators have even proposed that AD may begin in the OB due to pathogens entering via peripheral olfactory apparatus. Mann, *Mech. Ageing Dev.,* 1988, January 42(1) 1-15. It has also been reported that neurofibrillary tangles spread from the entorhinal cortex to the limbic system, then to cortical areas, according to Braak's stages. Kovacs, *Neuroreport.* 2001, Feb. 12, 12(2) 285-8. However, these hypotheses have been disputed. See Davies, supra and Kovacs, *Neuroreport.* 2001, Feb. 12, 12(2) 285-8.

In sum, because the olfactory bulb plays a key role in the cholinergic system in the cerebral cortex, damage to the olfactory bulb not only impairs the patient's sense of smell, it also impairs vital systems related to learning and memory due to disruption of the cholinergic systems.

Because of the role played in AD by inflammation, anti-inflammatory compounds have been identified as candidates for treating Alzheimer's Disease. However, the delivery of these compounds has generally been through an oral route, and the systemic side effects associated with long term use of these compounds are often undesirable.

Some investigators have proposed implanting an effective amount of nerve growth factor (NGF) in a sustained release device for treating Alzheimer's Disease. However, NGF simply helps restore damaged neurons—it does little to stop the damage from occurring.

Other have examined the possibility of intranasal installation of therapeutic peptides in the form of drops. However, it is not known whether significant amounts of these peptides are able to cross through the nasal mucosa and into the cerebral cortex.

SUMMARY OF THE INVENTION

The present invention is based upon the realization that the cribriform plate portion of the nasal cavity is substantially permeable to red light. Because of that permeability, therapeutic doses of red light may be non-invasively administered from the nasal cavity through the cribriform plate and through the OB of the prefrontal cortex of the brain. The resultant irradiation of the OB with red light is expected to have many beneficial effects upon a person suffering from AD.

It has been reported in the literature that near infra-red light saves neurons that have been challenged by neurotoxics from apoptosis. In particular, Wong-Riley, *J. Biol. Chem.* 2004, e-pub Nov. 22, reports that irradiating neurons with 670 nm red light significantly reduced neuronal cell death induced by 300 mM KCN from 83.6% to 43.5%.

The general concept of repairing brain cells through red light irradiation is also well supported by the literature. Wollman, *Neurol. Res.* 1998, July 20(5) 470-2 reports that providing daily 3.6 J/cm$^2$ doses of red light from a He-Ne laser to cortex explants resulting in a significant amount of sprouting of cellular processes outgrowth. Wollman concludes that the irradiation induces neurite processes sprouting and improves nerve tissue recovery. Similarly, Wollman,

*Neurol. Res.* 1996 October 18(5) 467-70 reports the enhanced migration and massive neurite sprouting of cultured rat embryonal brain cells subject to an 8 minute dose of a 0.3 mW, He—Ne laser. Therefore, the red light of the present invention may further cause repair and regeneration of damaged neuronal cells.

Therefore, it is expected that transmitting an effective amount of red light across the cribriform plate to the olfactory bulb will have both neuroprotective and neuroregenerative effects upon the olfactory bulb. The therapeutic benefits provided to the OB are expected to extend to its afferents, including enhanced BDNF supply and improved cholinergic transmission. Accordingly, learning and memory may be improved, or their deficits delayed.

Therefore, in accordance with the present invention, there is provided a method of treating a patient having an olfactory bulb, comprising:
a) irradiating the olfactory bulb with an effective amount of red light.

Also in accordance with the present invention, there is provided a method of treating or preventing Alzheimer's disease, comprising the steps of:
a) providing an implant having a red light source,
b) positioning the implant within a nasal cavity, and
c) activating the red light source to irradiate brain tissue with an amount of red light.

DESCRIPTION OF THE FIGURES

FIGS. 5a-5c disclose side, front and upper views of a red light emitting intranasal device of the present invention.

DETAILED DESCRIPTION OF THE INVENTION

Figure 1:
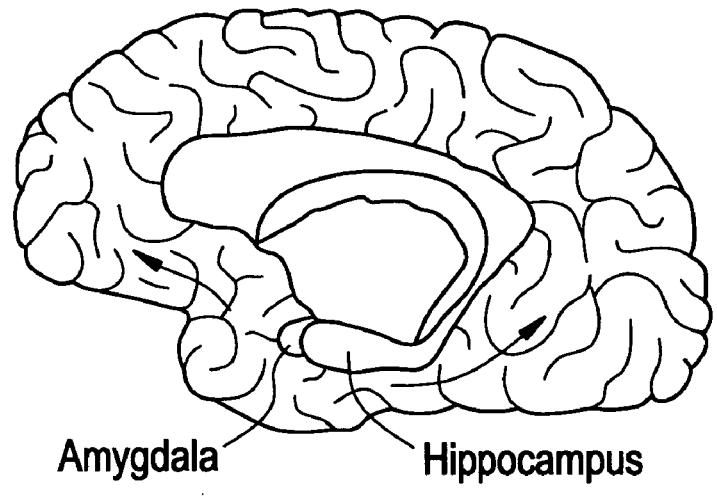
FIG. 1 discloses a saggital cross section of a brain afflicated with Alzheimer's Disease.

Now referring to FIG. 1, there is provided a saggital cross section of a brain afflicated with Alzheimer's Disease. In general, the disease begins in the hippocampus, spreads to the amydgala, and proceeds anteriorly to the prefrontal cortex.

Figure 2:
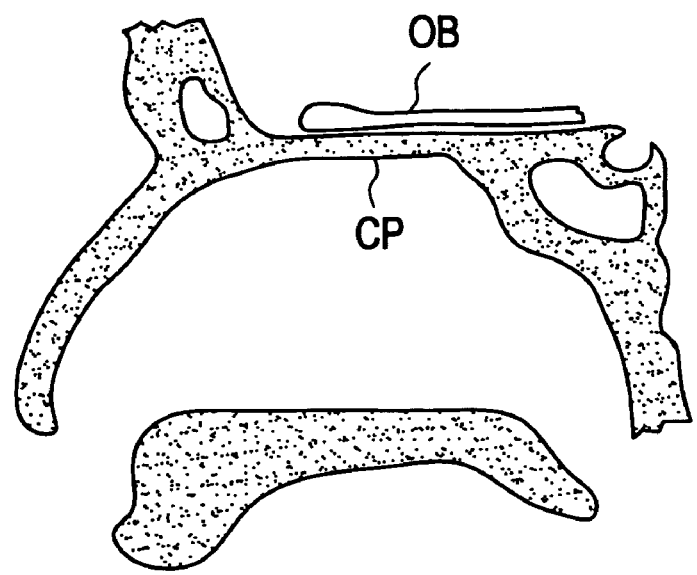
FIG. 2 discloses a cross-sectional side view of the nasal cavity, wherein the cribriform plate is a wafer-thin ledge of porous bony tissue.

Now referring to FIG. 2, the cribriform plate CP is a wafer-thin ledge of porous bony tissue located beneath the prefrontal cortex portion of the brain and above the nasal cavity. The porosity of the cribriform plate is filled with olfactory nerves extending from the olfactory bulb OB (located at the lower base of the brain) and terminating within the nasal mucosa. As shown here, the cribriform plate has a thickness of about 1 mm while the olfactory bulb has a thickness of about 3 mm. Thus, red light will traverse 1 mm of nerve fiber tissue within the cribriform plate and 3 mm of grey matter associated with the olfactory bulb, totaling to about 4 mm.

Figure 3:
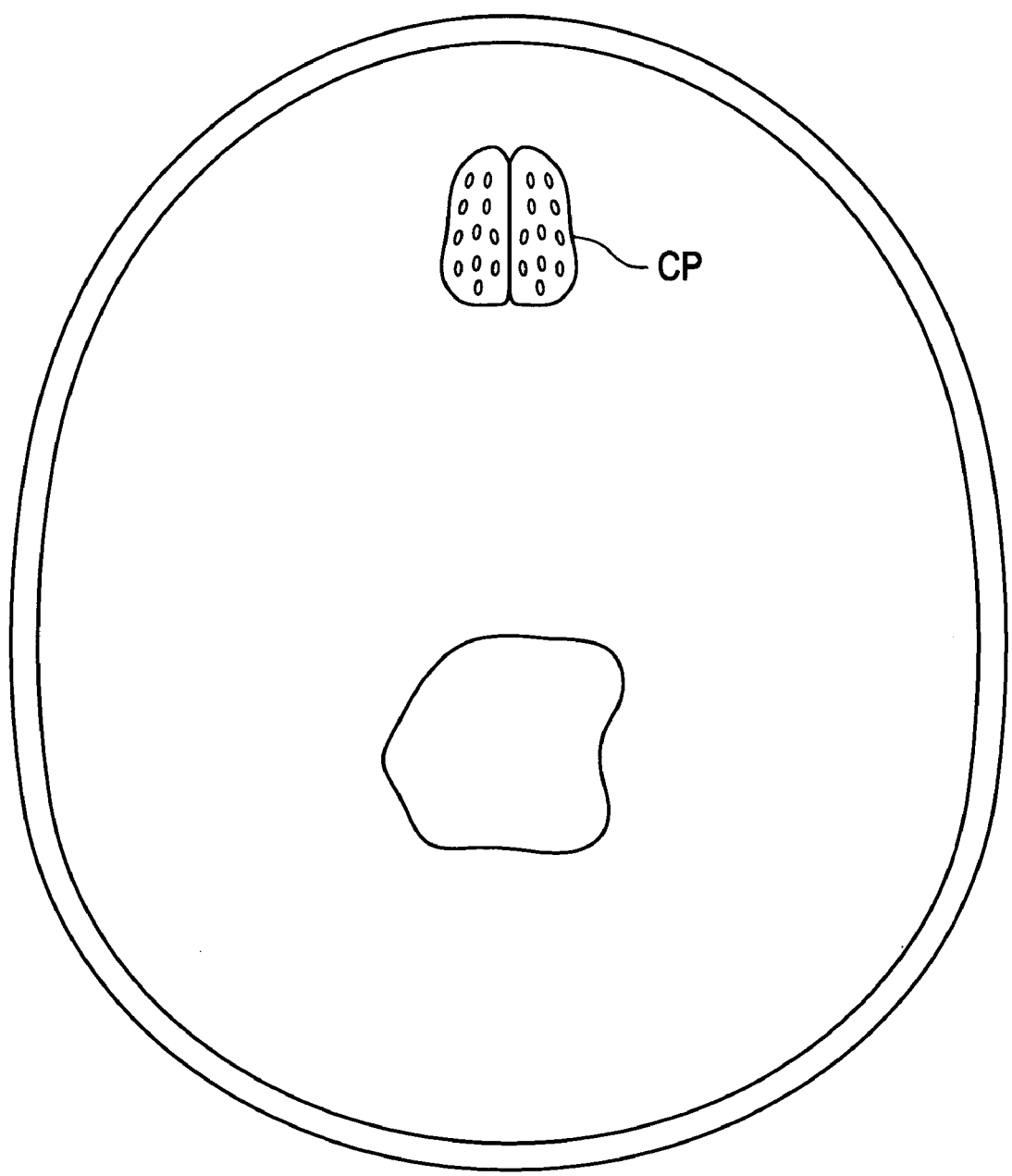
FIG. 3 discloses a coronal view of the cribriform plate.

Now referring to FIG. 3, the coronal view of the cribriform plate CP reveals that fairly large throughholes extend transversely through about one-half of the cribriform plate. These throughholes comprises about 50 areal % of the cribriform plate.

Figure 4:
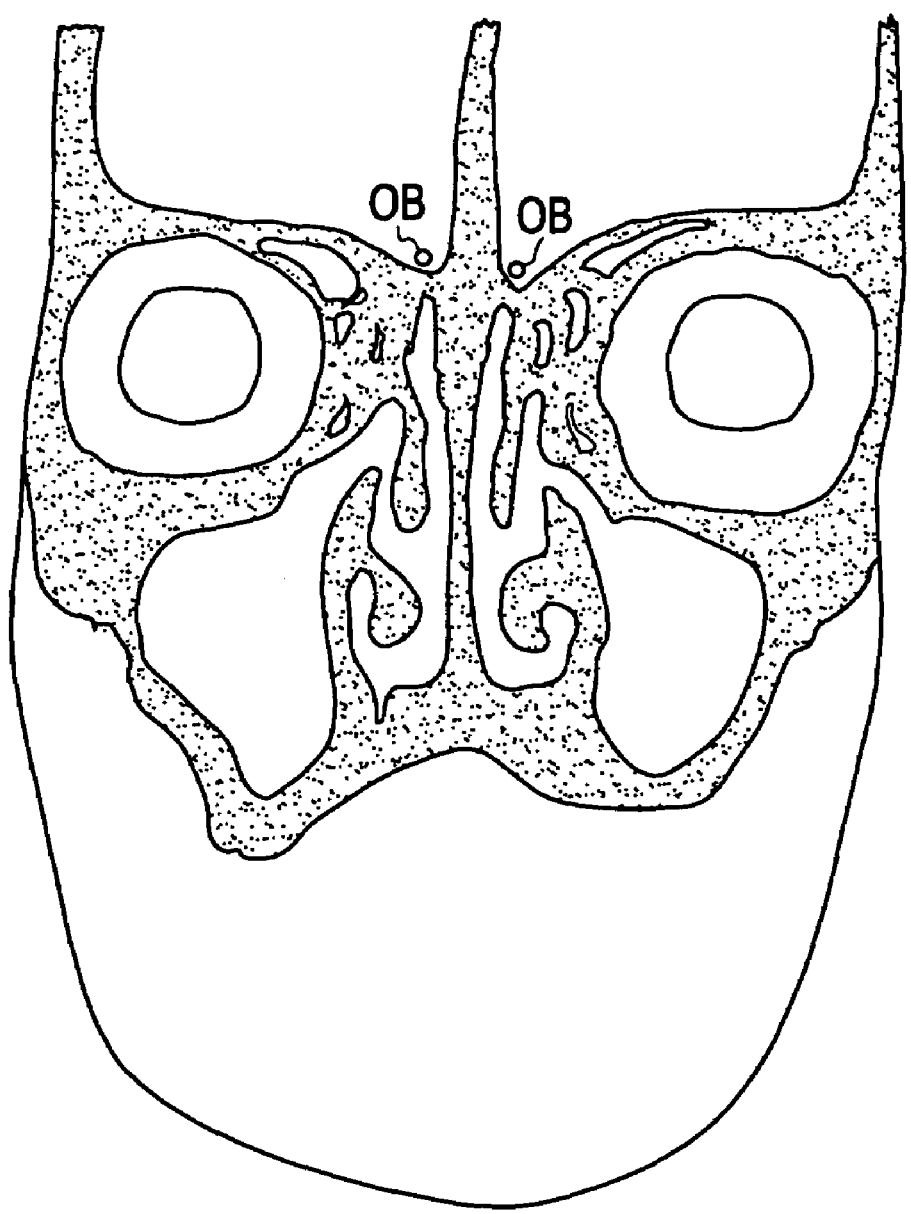
FIG. 4, this frontal cross-section of the skull.

Now referring to FIG. 4, this frontal cross-section shows that the thickness cribriform plate and the olfactory bulb comprise only about two mm.

Therefore, since about one half of the face of the cribriform plate comprises porosity filled with light-permeable nervous tissue, red light shined through the cribriform plate from the nasal cavity will encounter only soft, light permeable nervous tissue about half of the time. Because red light can penetrate gray matter to a depth of up to a centimeter, portions of the prefrontal cortex as deep as about one centimeter can be irradiated with red light. In instances wherein the combined thickness of the cribriform plate and olfactory bulb are less than about 1 cm, portions of the prefrontal cortex may also be therapeutically irradiated.

Moreover, since red light experiences high diffraction as it proceeds through soft tissue, it is possible for the entire lower portion of the prefrontal cortex to be irradiated with red light.

Therefore, in accordance with the present invention, there is provided a method of treating or preventing Alzheimer's disease, comprising the steps of:
a) providing an device having a fiber optic and a red light source,
b) positioning the fiber optic within a nasal cavity, and
c) activating the red light source to irradiate brain tissue with an effective amount of red light.

Without wishing to be tied to a theory, it is believed that the therapeutic neuroprotective and neuroregenerative effects of red light described above may be due to a) an increase in ATP production in the irradiated neurons, and b) an increase in the activity of local anti-oxidant enzymes superoxide dismutase (SOD) and catalase.

It is believed that irradiating neurons in the brain with red light will likely increase ATP production from those neurons. Mochizuki-Oda, *Neurosci. Lett.* 323 (2002) 208-210, examined the effect of red light on energy metabolism of the rat brain and found that irradiating neurons with 4.8 W/Cm$^2$ of 830 nm red light increased ATP production in those neurons by about 19%.

Without wishing to be tied to a theory, it is further believed that the irradiation-induced increase in ATP production in neuronal cell may be due to an upregulation of cytochrome oxidase activity in those cells. Cytochrome oxidase (also known as complex IV) is a major photoacceptor in the human brain. According to Wong-Riley, *Neuroreport,* 12:3033-3037, 2001, in vivo, light close to and in the near-infrared range is primarily absorbed by only two compounds in the mammalian brain, cytochrome oxidase and hemoglobin. Cytochrome oxidase is an important energy-generating enzyme critical for the proper functioning of neurons. The level of energy metabolism in neurons is closely coupled to their functional ability, and cytochrome oxidase has proven to be a sensitive and reliable marker of neuronal activity.

Importantly, the literature has made a direct association between defects in cytochrome c oxidase and Alzheimer's Disease. See, e.g., Cottrell, Neuropathol. Appl. Neurobiol. 2002, October 28(5) 3906; Cottrell, *Neurology,* July 24, 57(2) 260-4. Alieu, *Neurol. Res.,* 2003, September 25(6) 665-74. Aliev, *Ann NY Acad. Sci.,* 2002, November 977, 45-64.

By increasing the energetic activity of cytochrome oxidase, the energy level associated with neuronal metabolism may be beneficially increased. Indeed, the literature reports that red light reverses the inhibitory effects of neurotoxins upon cytochrome oxidase activity, leading to increased energy metabolism in neurons functionally inactivated by toxins. Wong-Riley *Neuroreport* 12(14) 2001:3033-3037 and Wong-Riley, *J. Biol. Chem.,* e-pub, Nov. 22, 2004.

According to Kamanli, *Cell Biochem. Func.* 2004, 22:53-57, catalase detoxifies hydrogen peroxide and converts lipid hydroperoxides into non-toxic alcohols, and is essential for the inhibition of inflammation related to the function of neutrophils.

Romm, *Biull. Eksp. Biol. Med.* 1986 October 102(10) 426-8 reports that laser irradiation of wounds results in a decreased chemiluminescence that is attributable to activation of catalase in the tissue fluid.

Therefore, it is believed that irradiating the AD brain with an effective amount of red light will therapeutically increase of the activity of catalase in the irradiated region, thereby attenuating the deleterious effect of hydrogen peroxide upon the neurons in the AD brain.

According to Kamanli, supra, SOD catalyses dismutation of the superoxide anion into hydrogen peroxide.

The literature repeatedly reports that red light irradiation of inactivated SOD increases its activity. For example, Vladimirov, Biochemistry (Moscow) 69(1) 2004, 81-90 provides a review including the photoreactivation of Cu—Zn SOD under He—Ne laser. Karu, *Laser Ther.* 1993, 5, 103-9 reports that reactive oxygen species in human blood were found to be suppressed after laser diode illumination at 660 nm, 820 nm, 880 nm and 950 nm. This affect has been attributed by other authors to the activation of SOD or catalase. Volotovskaia *Vopr Kurortol Zizioter Lech Fiz Kult* 2003 May-June(3)22-5 reports that 632 nm He—Ne laser irradiation of blood has an anti-oxidant effect as shown by activation of SOD. Ostrakhovich Vestn Ross Akad Med Nauk. 2001(5) 23-7 reports that infrared pulse laser therapy of RA patients caused an increase in SOD activity. Gorbatenkova *Biofizika,* 1988 July-August 33(4) 717-9 reports that SOD that was inactivated by hydrogen peroxide was reactivated by a 450-680 nm red light laser Vladimirov, *Free Rad. Biol. Med.* 1988, 5(5-6) 281-6 reports the inactivation of SOD by its incubation in a low pH 5.9 solution and its subsequent reactivation by helium-neon light. Catalase was found to be reactivated as well. Cho, *In Vivo,* 2004, September-October 18(5) 585-91 reports on the use of low level laser therapy (LLLT) to treat knee joints that have been induced with OA by injection of hydrogen peroxide. SOD was reported to increase about 40% in the OA group as compared to controls.

Therefore, it is believed that irradiating the AD brain with an effective amount of red light will therapeutically increase of the activity of SOD in the irradiated region, thereby attenuating the deleterious effect of superoxide anion upon the neurons in the AD brain.

According to Leung, *Laser Surg. Med.* 31:283-288 (2002), nitric oxide enhances oxidative insult by reacting with superoxide anion to form a stronger oxidant, peroxynitrite, which leads to mitochondrial dysfunction, DNA damage and apoptosis. Haas, *Neuroscience Letters,* 322,(2002) 121-126 reports that iNOS is induced by amyloid plaques in AD brains, and is responsible for producing NO, which is considered to be highly neurotoxic when generated in excess.

Leung, supra, investigated the effect of low energy red laser after stroke in rats, and found that red light can suppress NO synthase activity. In particular, Leung found that irradiating a portion of the rat's brain with a 660 nm red light (average power 8.8 mW, 2.64 $J/cm^2$) reduced NOS activity up to about $^{80}$% over that in unirradiated stroke rats, and up to about 60% over the NOS activity in normal rats. Leung concluded that the main findings of the study was that low energy laser may be protective by suppressing the activity of NOS in cerebral ischemia and reperfusion.

Without wishing to be theory, it is believed that irradiation of a portion of an Alzheimer's brain will similarly therapeutically suppress NO synthase activity, thereby attenuating peroxynitrite activity.

It is noted that Leung, supra, also reported that red light irradiation of the brain resulted in a TGF-β tissue concentration of 1-6 ng/ug protein of tissue. Thus, red light irradiation of the OB may very well be an attractive non-invasive way of generating large amounts of TGF-β within the brain.

Moreover, the literature has reported other highly beneficial effects of red light, including its attenuation of the immune response following neuronal injury. Byrnes, *Lasers Surg. Medicine* 9999:1-15(2005) reports that 810 nm light promotes the regeneration and functional recovery of the injured spinal cord, and significantly suppressed IL-6 and iNOS expression and immune cell activation. Of note, Byrnes reports a 171-fold decrease in IL-6 expression and an 80% reduction in iNOS expression when the spinal cord lesion was irradiated on a daily basis with about 100 $J/cm^2$ red light for about 2 weeks.

The ability of red light to suppress IL-6 in injured neuronal matter is important to the present invention because IL-6 is thought to play a major role in AD pathology. For example, Del Bo, *Neuroscience Letters* 188 (1995) 70-74 reports that IL-6 increased mRNA levels of beta-amyloid precursor protein (APP) in a dose dependent relationship. Oiu, *J. Neuroimmunology,* 139, (2003) 51-57 reports that IL-6 is thought to contribute to AD by increasing amyloidogenesis. Huell, *Acta Neuropathol.* (Berl) 1995; 89(6) 544-51 reports that IL-6 is found in early stages of plaque formation and is restricted to the brain of AD patients. In sum, it appears that IL-6 plays and early role in the pathology of AD. Therefore, reducing the IL-6 expression in and around AD lesions may be quite helpful.

Also without wishing to be tied to a theory, it is further believed that red light may also be effective in causing the release of calcitonin gene related peptide (CGRP), which in turn may cause mast cells to degranulate and release IL-10, thereby attenuating AD.

Preferably, the red light of the present invention has a wavelength of between about 650 nm and about 1000 nm. In some embodiments, the wavelength of light is between 800 and 900 nm, more preferably between 800 nm and 835 nm. In this range, red light has not only a large penetration depth (thereby facilitating its transfer to the fiber optic and SN), but Wong-Riley reports that cytochrome oxidase activity is significantly increased at 830 nm, and Mochizuki-Oda reported increased ATP production via a 830 mn laser.

In some embodiments, the wavelength of light is between 600 and 700 nm. In this range, Wong-Riley reports that cytochrome oxidase activity was significantly increased at 670 nm. Wollman reports neuroregenerative effects with a 632 nm He—Ne laser.

Respecting penetration depths, Byrnes, *Lasers Surg. Medicine* 9999:1-15(2005) reports that an effective amount of 810 nm light was able to traverse a 1 cm thick rat spinal cord. The penetration depths of various wavelengths of red light in grey matter brain tissue have been reported in Yaroslavsky, *Phys. Med. Biol.* 47(2002) 2059-73 as follows:

| Wavelength | Penetration Depth (mm) |
|---|---|
| 630 nm | 0.83-4.06 |
| 675 nm | 1.29 |
| 670 nm | 4.4 |
| 1064 nm | 1.18-3.28 |

In some embodiments, the light source is situated to irradiate adjacent tissue with between about 0.02 J/cm$^2$ and 200 J/cm$^2$ energy. Without wishing to be tied to a theory, it is believed that light transmission in this energy range will be sufficient to increase the activity of the cytochrome oxidase and anti-oxidant activity around and in the OB. In some embodiments, the light source is situated to irradiate target tissue with more than 10 J/cm$^2$, and preferably about 100 J/cm$^2$ energy. In some embodiments, the light source is situated to irradiate adjacent tissue with between about 0.2 J/cm$^2$ and 50 J/cm$^2$ energy, more preferably between about 1 J/cm$^2$ and 10 J/cm$^2$ energy.

In some embodiments, the light source is situated to produce an energy intensity of between 0.1 watts/cm$^2$ and 10 watts/cm$^2$. In some embodiments, the light source is situated to produce about 1 milliwatt/cm$^2$.

Of note, it has been reported that the neuroprotective effects of red light can be effected by a single irradiation on the order of minutes. Wong-Riley, *J. Biol. Chem.* 2004, e-pub November 22, reports that irradiating neurons with 670 nm red light for only ten minutes results in neuroprotection. Similarly, Wong-Riley *Neuroreport* 12(14) 2001: 3033-3037 reports that a mere 80 second dose of red light irradiation of neuron provided sustained levels of cytochrome oxidase activity in those neurons over a 24 hour period. Wong-Riley hypothesizes that this phenomenon occurs because "a cascade of events must have been initiated by the high initial absorption of light by the enzyme".

Therefore, in some embodiments of the present invention, the therapeutic dose of red light is provided on approximately a daily basis, preferably no more than 3 times a day, more preferably no more than twice a day, more preferably once a day.

In some embodiments, the red light irradiation is delivered in a continuous manner. In others, the red light irradiation is pulsed in order to reduce the heat associated with the irradiation. Without wishing to be tied to a theory, it is believed that pulsed light may be more effective in achieving the vibratory oscillation of the catalase and SOD molecules.

In some embodiments, red light is combined with polychrome visible or white light.

Figure 5C:
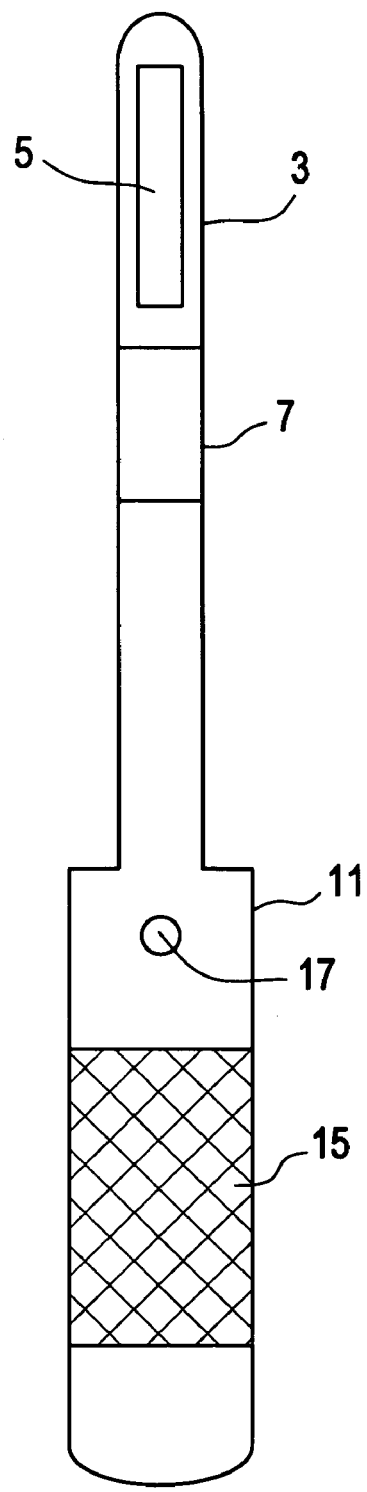

Now referring to FIGS. 5a-5c, there is provided a probe 1 for treating a neurodegenerative disease in a patient, comprising:
a) a distal portion 3 adapted to fit within an upper portion of a nasal cavity and having a red light emitter 5 oriented towards the cribriform plate,
b) a flexible intermediate portion 7 having an angled, narrowed portion 9,
c) a proximal portion 11 having a handgrip 13 having a knurled surface 15 and a red light activation button 17,
d) a red light source (not shown),
e) a fiber optic cable (not shown) connecting the red light source and the red light emitter.

In some embodiments, the height of the distal portion is greater than its width. This allows orientation. In some embodiments, the distal portion is detachable from the remainder of the device. This allows it to be periodically cleaned by the user. In some embodiments, the tip of the distal portion is rounded in order to ease the entry of the distal portion in the nasal passage. In some embodiments, the length of the distal portion corresponds substantially to the length of the cribriform plate. This allows the red light emitter to emit light along substantially the entire porosity of the cribriform plate. In some embodiments, the length of the red light emitter corresponds substantially to the length of the cribriform plate. In some embodiments, the red light emitter is oriented to face the cribriform plate upon insertion in the nasal passage. In some embodiments, the distal portion has an upper surface oriented to face the cribriform plate upon insertion. In some embodiments, the red light emitter emits light in an arc of less than 180 degrees. In some embodiments, the red light emitter emits light substantially lateral to the longitudinal axis of the proximal portion.

In some embodiments, the narrowed portion is provided along only one axis, thereby providing preferred bending.

In some embodiments, the red light source is located in the proximal portion. In some embodiments, the red light source is located in the distal portion. In some embodiments, the red light source is operated by a battery contained within the device. In some embodiments, the red light source is operated by an electric power cord connected to the device.

In some embodiments, a light reflective surface is provided around the red light emitter to concentrate the light.

Therefore, in accordance with the present invention, there is provided a probe for treating a neurodegenerative disease in a patient, comprising:
a) a proximal portion adapted to fit within a portion of a nasal cavity and having a red light emitter,
b) a distal portion having a handgrip having a knurled surface and a red light activation button, and
c) a red light source.

It has also been noticed by the inventors that the sphenoidal sinus of the nasal cavity lies adjacent important structures in the brain. The present inventors believe that irradiation of this sinus structure will allow for the therapeutic transmission of red light from the sphenoidal sinus to brain structures that may be affected by Alzheimer's Disease.

Therefore, in accordance with the present invention, there is provided a method of treating a patient having an neurodegenerative disease, comprising the step of:
a) irradiating a portion of a sphenoidal sinus with an effective amount of red light.

Figure 6:
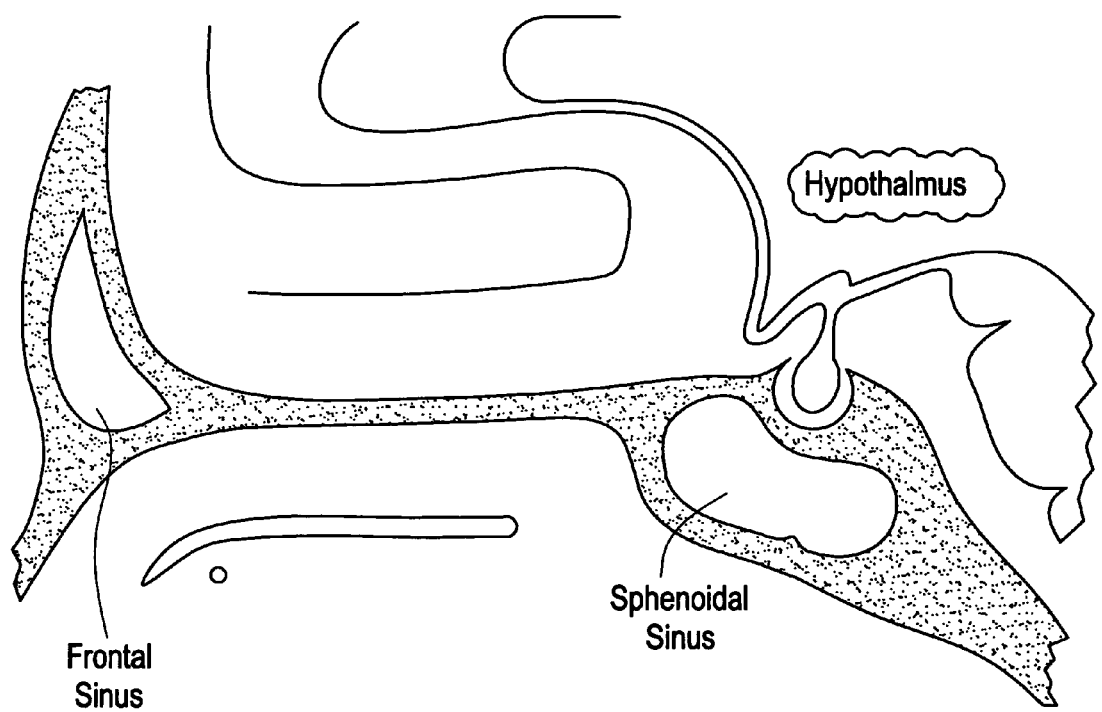
FIG. 6 is a medial cross-section of the cerebrum showing the adjacency of the sphenoidal sinus and the hypothalamus.

Now referring to FIG. 6, the upper wall that defines the sphenoidal sinus lies just below and slightly anterior to the hypothalamus. Accordingly, directing red light from the interior of the sinus in the direction of the upper wall will cause light to traverse that upper wall and penetrate hypothalamic tissue and provide a therapeutic benefit thereto.

Therefore, in accordance with the present invention, there is provided a method of treating a patient having a hypothalamus, comprising the step of:

a) irradiating the hypothalamus with an effective amount of red light.

Figure 7:
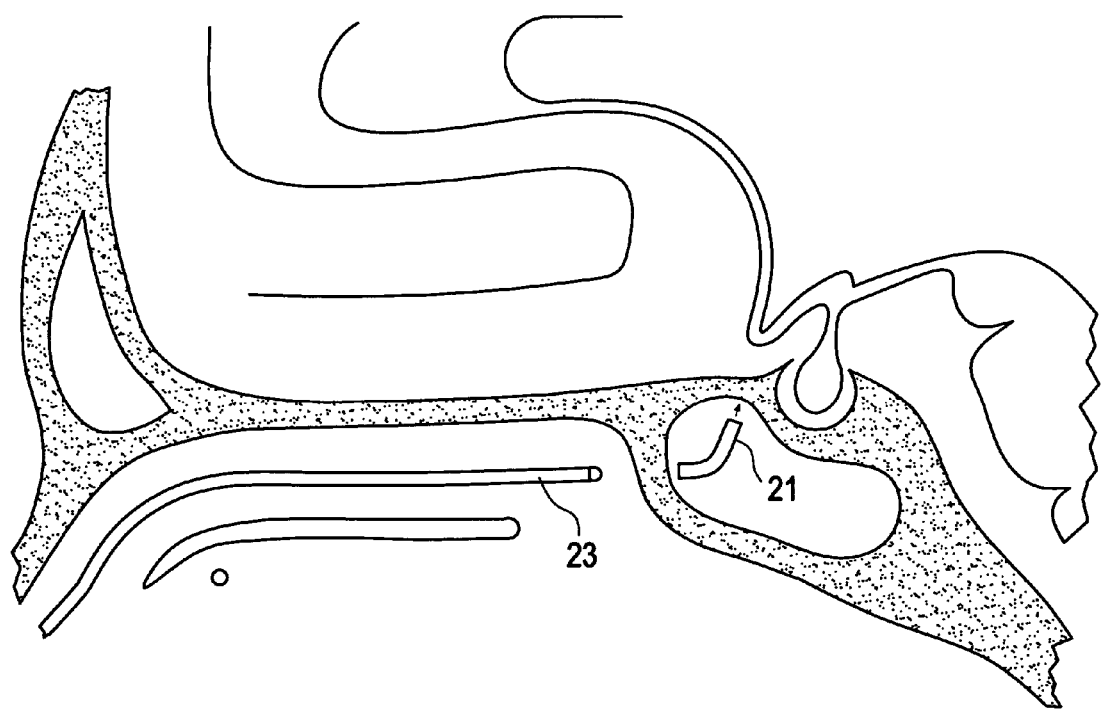
FIG. 7 shows a catheter of the present invention inserted into the sphenoidal sinus and irradiating the hypothalamus.

Preferably, light is directed to the sinus by the use of a catheter containing a fiber optic cable, whereby the catheter can be directed under fluoroscopy from the nasal cavity through the opening of the sphenoidal sinus and into the sinus. The fiber optic cable at the proximal end of the catheter may be connected to a red light source, while the distal end of the fiber optic is adapted to emit the red light. In some embodiments, red light exits the distal end of the catheter in a substantially axial fashion. Accordingly, now referring to FIG. 7, in these embodiments, the axis of the distal end portion 21 of the fiber optic cable 23 should be directed at the hypothalamus.

Figure 8:
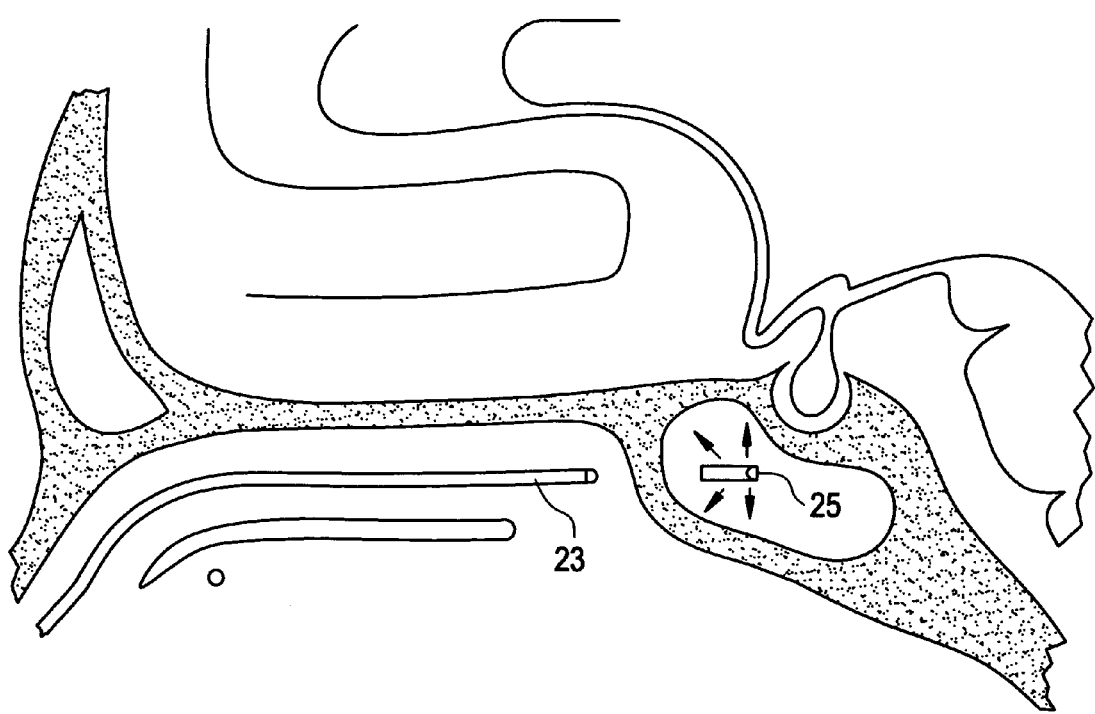
FIG. 8 shows a catheter of the present invention inserted into the sphenoidal sinus and diffusing light in a plurality of direction.

In some embodiments, the distal end of the catheter is adapted with a diffuser to diffuse the red light in a plurality of directions. Accordingly, the distal end of this catheter need not be directed at the hypothalamus in order to convey red light thereto. In some embodiments thereof, as now referring to FIG. 8, the distal end of the fiber optic is equipped with a convex reflective surface 25 pointing in the proximal direction. Red light entering the distal end portion of the fiber optic reflects off the reflective surface in all radial directions, thereby irradiating the desired portion of the sphenoidal sinus and hypothalamus.

Figure 9:
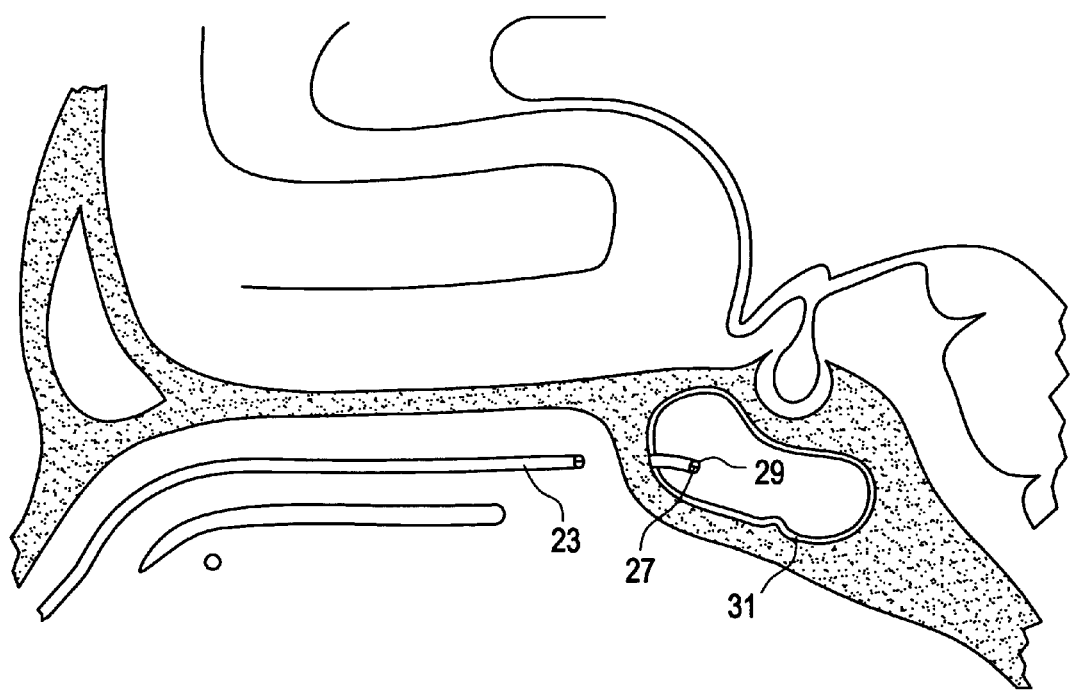
FIG. 9 shows a catheter of the present invention inserted into the sphenoidal sinus and having an inflated balloon.

Now referring to FIG. 9, in one embodiment, the catheter 23 entering the sphenoidal sinus is equipped with a dual lumen catheter having a red light fiber optic 27 housed in a first lumen. The distal end of the second lumen 29 is attached to a deflated balloon having a partially reflective surface, while the proximal end of the second lumen is attached to a source of air. When the dual lumen catheter is inserted into the sphenoidal sinus, the air source is activated, thereby inflating the balloon 31 to conform with the contour of the sphenoidal sinus. Thereafter, delivery of red light to the distal end of the fiber optic has the effect of irradiating the entire surface of the balloon, thereby irradiating substantially all of the the sphenoidal sinus and therefore the hypothalamus.

Figure 10:
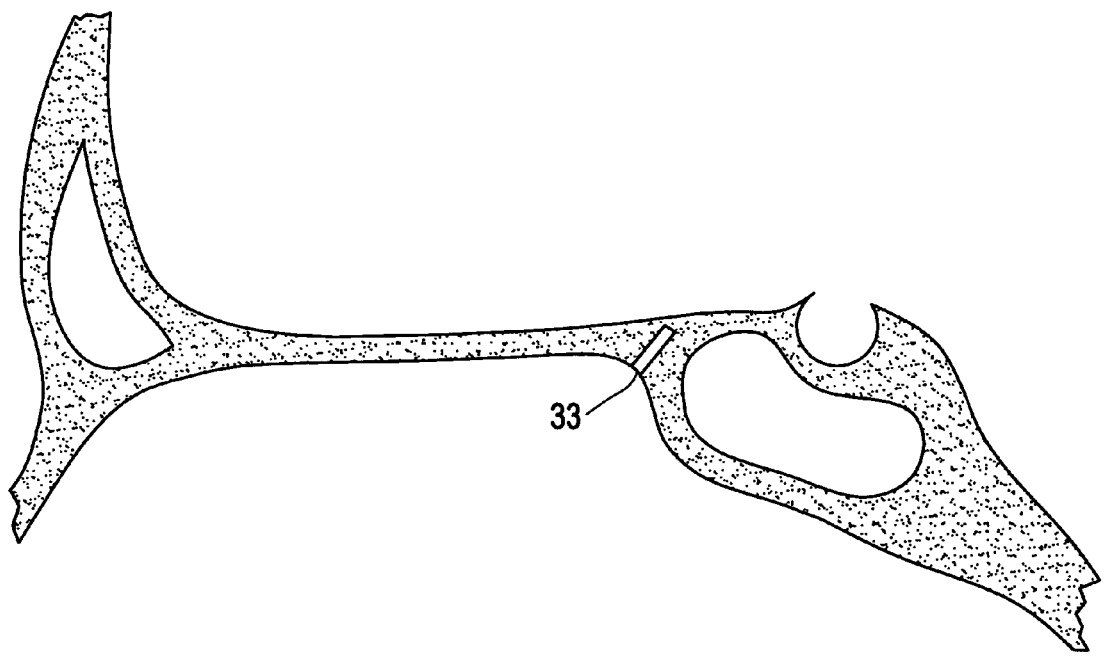
FIG. 10 shows a light transmissive pin of the present invention inserted into bone adjacent the sphenoidal sinus and oriented towards the hypothalamus.

Now referring to FIG. 10, in some embodiments, a light transmissive pin 33 in inserted into the upper wall of the nasal cavity substantially at the junction between the cribriform plate and the anterior wall of the sphenoidal sinus. The pin is oriented to point substantially in the direction of the hypothalamus. Because the pin is light transmissive, there is substantially no absorption of the as light travels through the pin. Delivery of red light to the proximal end of the pin travels through the pin and exits the distal end of the pin. When light exits the distal end of the pin, it travels in a substantially axial direction substantially directly at the hypothalamus.

Preferably, the pin has a glass core a threaded outer surface comprising a light reflective material. In preferred embodiments, the pin is a metallic screw having an axial throughbore bore filled with glass or a red light transmissive polymer.

Therefore, in accordance with the present invention, there is provided a method of treating a patient having an neurodegenerative disease, comprising the step of:

a) placing a red light transmissive pin in a bony portion of a nasal cavity, and b) directing red light through the pin.

Another brain structure intimately associated with Alzheimer's Disease is the amydgala. The amydgala is part of the limbic system and is located substantially near the inner medial surface of the lower portion of the temporal lobe of the brain. It is located slightly medial to the anterior portion of the hippocampus. The amydgala plays a major role in many important CNS functions, including control of emotions. It has been reported that the amydgala is often one of the first structures affected by Alzheimer's Disease, with degeneration appearing slightly after degeneration of the hippocampus.

Figure 11:
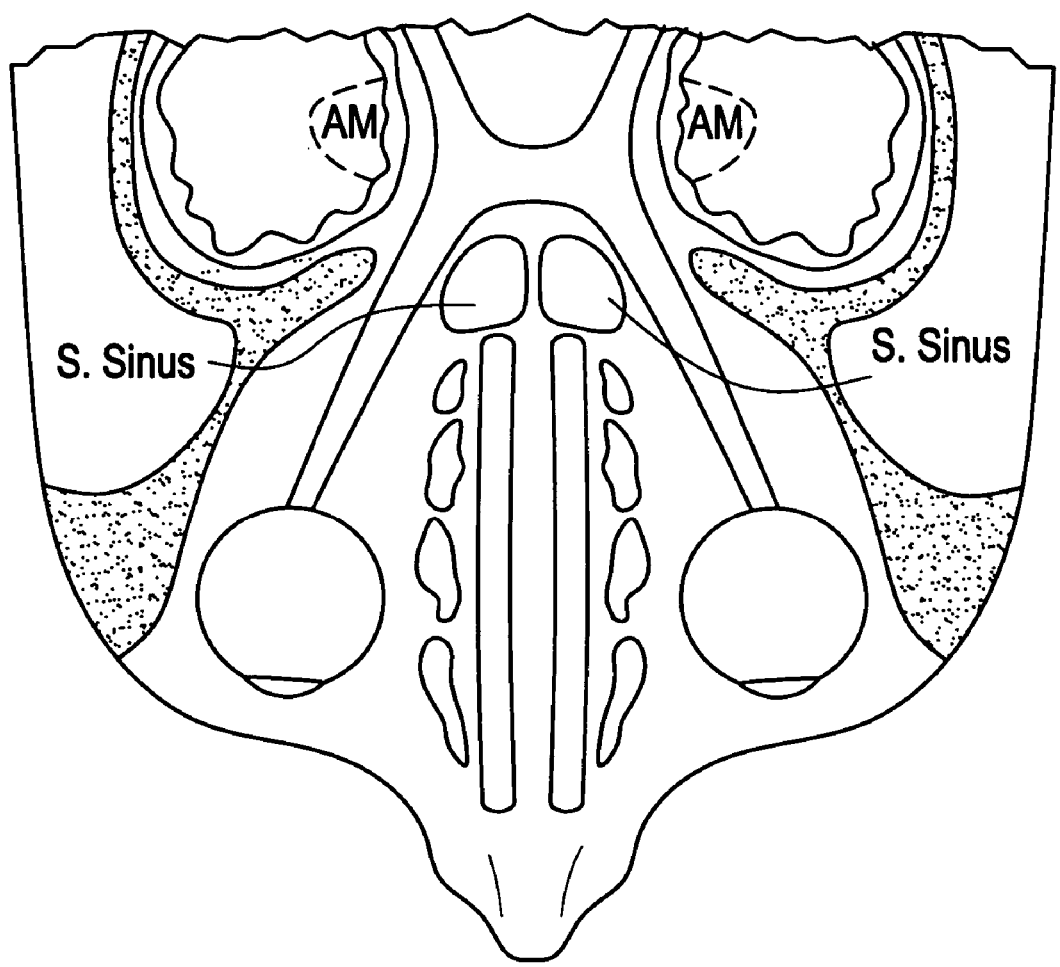
FIG. 11 shows a horizontal section of the head showing the adjacency of the sphenoidal sinus and the medial surface of the temporal lobe.

Now referring to FIG. 11, it has further been noticed by the present inventors that the amydgala AM resides substantially lateral to and slightly posterior to the sphenoidal sinus, and is separated from the sphenoidal sinus only by the thin optic nerve.

Accordingly, the present inventors believe that the sphenoidal sinus may be used as a base for a red light emitting catheter or implant that can direct therapeutic amounts of red light to the amydgala.

In some embodiments, the preferred catheters described above for irradiating the hypothalamus may also be used to irradiate the amydgala.

Therefore, in accordance with the present invention, there is provided a method of treating a patient having an amydgala, comprising the step of:

a) irradiating the amydgala with an effective amount of red light.

Now referring back to FIG. 6, it has further been noticed by the present inventors that the frontal sinus abuts a large portion of the basal prefrontal cortex. Accordingly, the present inventors believe that the frontal sinus may be used as a base for a red light emitting catheter that can direct therapeutic amounts of red light to the anterior portion of the basal prefrontal cortex. In some embodiments, the preferred catheters described above for irradiating the hypothalamus may also be inserted into the frontal sinus and used to irradiate the basal prefrontal cortex.

Figure 12:
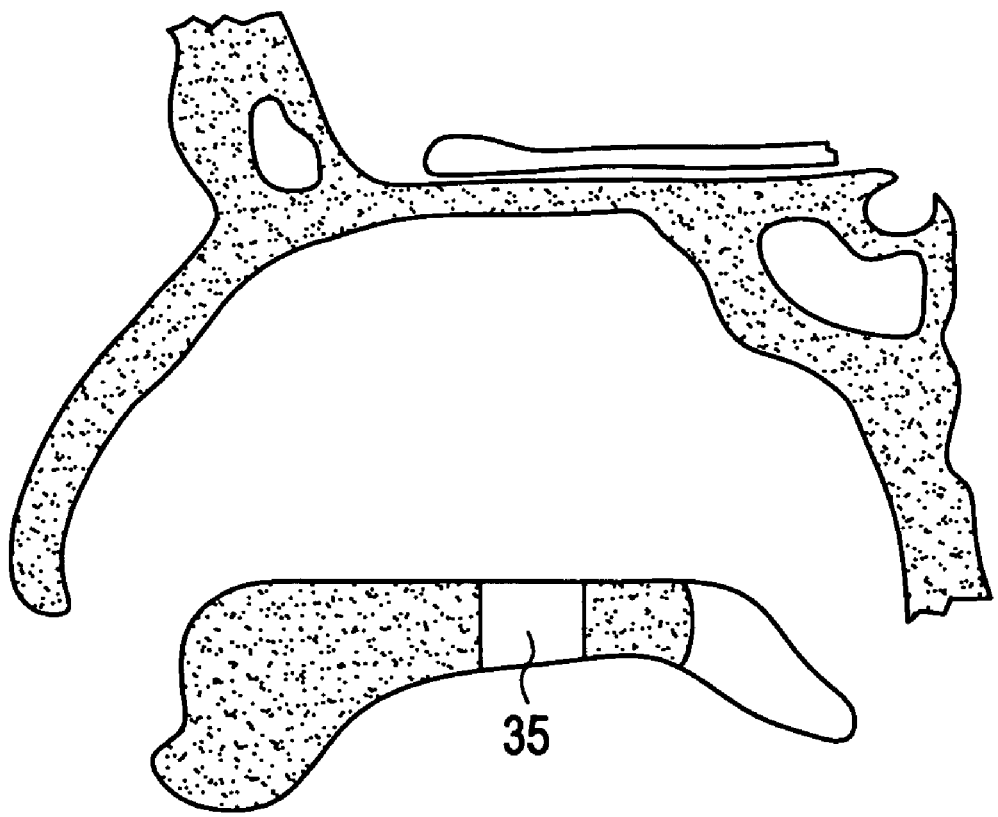
FIG. 12 shows a cross-section in which a light-transmissive pin of the present invention inserted into the bone in the roof of the mouth.

In another embodiment, as in FIG. 12, a transmissive pin 35 is positioned through the palantine bone located on the floor of the nasal cavity (the inferior nasal concha). In use, a red light source may be placed in the mouth and red light is shined through the transmissive pin. Because the axis of the pin is directed to the cribriform plate, red light is shined from the mouth and through the cribriform plate to the olfactory bulb.

Therefore, in accordance with the present invention, there is provided a method of treating or preventing Alzheimer's disease, comprising the steps of:

a) providing an implant having a red light source, b) positioning the implant within a nasal cavity, and c) activating the red light source to irradiate brain tissue with an amount of red light.

In some embodiments, red light is provided via an implant implanted within the sphenoidal sinus.

Figure 13A:
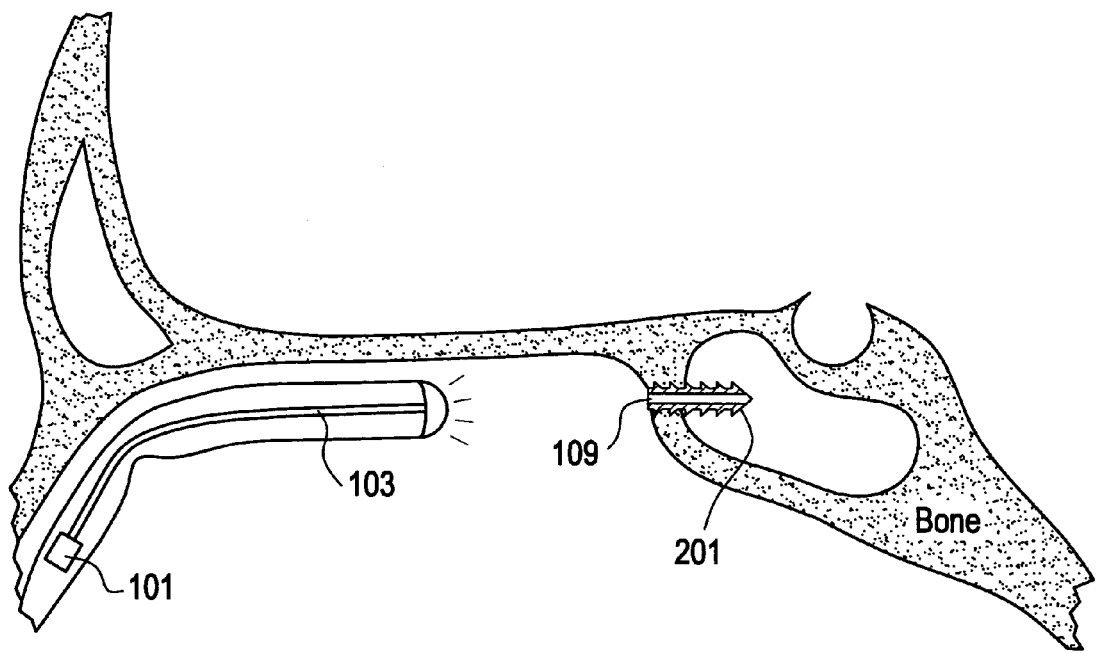
FIGS. 13a&b represent cross-sections of an implant of the present invention implanted within the sphenoidal sinus.

In some embodiments, the implant is simply a light conduit that allows red light to travel from the nasal cavity outside the sphenoidal sinus, through the sphenoidal sinus and into the brain. Now referring to FIG. 13a, there is provided a first exemplary red light conduit implant having an external red light source. Externally based-control device has a red light source 101 for generating red light within the implanted device. The light generated by this source is transmitted through fiber optic cable 103 through the patient's nasal cavity to an internally-based light conduit 109 provided on the implant 201. In some embodiments, portions of the outer surface of the light conduit are coated with a reflective material 111.

Figure 13B:
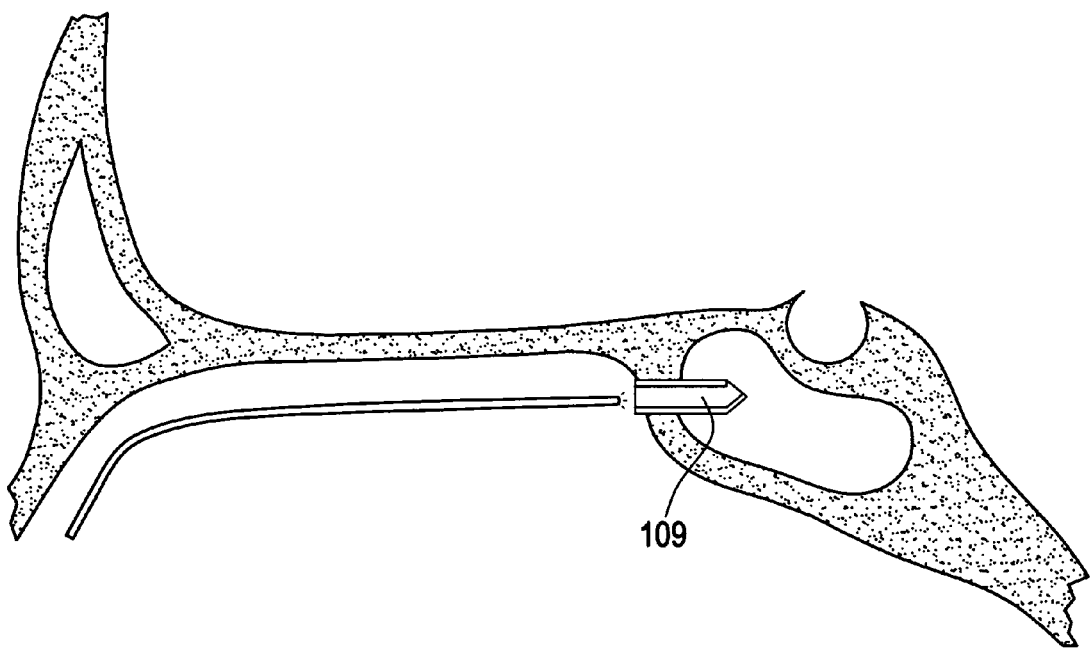

Now referring to FIG. 13b, there is provided another implant embodiment, wherein the red light exits the conduit at an angle.

Figure 14:
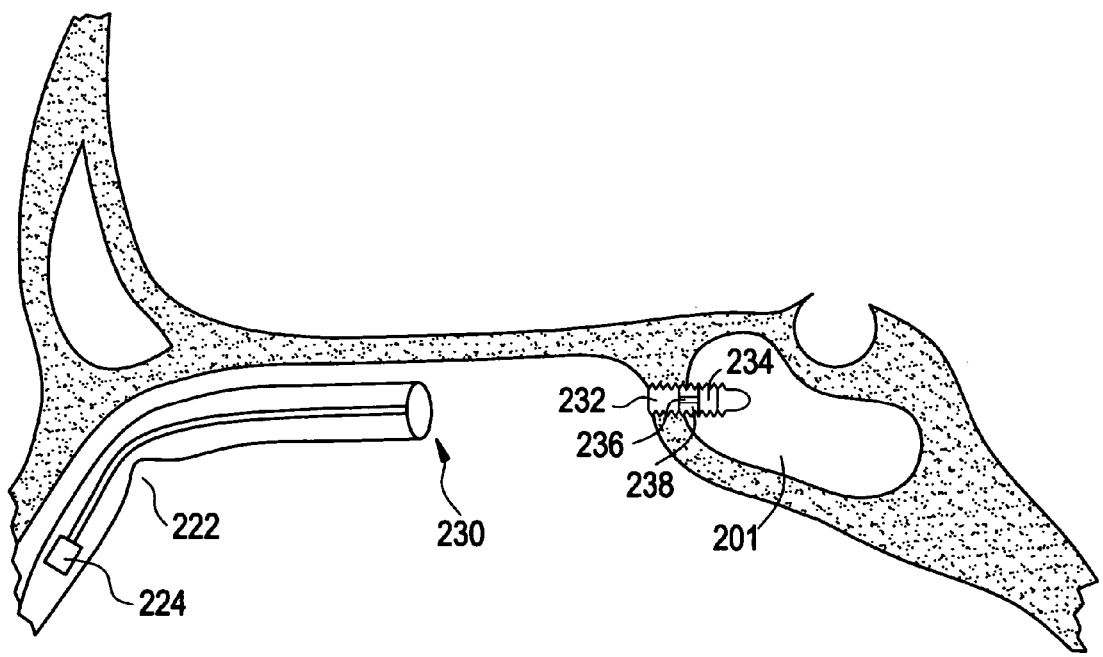
FIG. 14 represents a cross-section of an implant of the present invention having a red light LED and implanted within the sphenoidal sinus.

Now referring to FIG. 14, there is provided a second exemplary red light unit having an internal red light source. Internally-based energy device 222 has an RF energy source 224 and an antenna 230 for transmitting signals to an internally-based antenna 232 provided on the implant 201. These antennae 230, 232 may be electro-magnetically coupled to each other. The internal antenna 232 sends electrical power through a conductor 236 situated within an insulator 238 to a red light emitting diode (LED) 234 disposed internally within the implant in response to the transmitted signal transmitted by the external antenna 230. The red light generated by the LED travels through the translucent distal portion 231 of the implant, across the sphenoidal sinus and into the brain.

In some embodiments, the telemetry portion of the device is provided by conventional, commercially-available components. For example, the externally-based power control device can be any conventional transmitter, preferably capable of transmitting at least about 40 milliwatts of energy to the internally-based antenna. Examples of such commercially available transmitters include Microstrain, Inc. Burlington, Vt. Likewise, the internally-based power antenna can be any conventional antenna capable of producing at least about 40 milliwatts of energy in response to coupling with the externally-generated Rf signal. Examples of such commercially available antennae include those used in the Microstrain Strinlink™ device. Conventional transmitter-receiver telemetry is capable of transmitting up to about 500 milliwatts of energy to the internally-based antenna.

In some embodiments, the implant further contains an internal power source, such as a battery (not shown), which is controlled by an internal receiver and has sufficient energy stored therein to deliver electrical power to the red light source of the implant in an amount sufficient to cause the desired effect.

Figure 15:
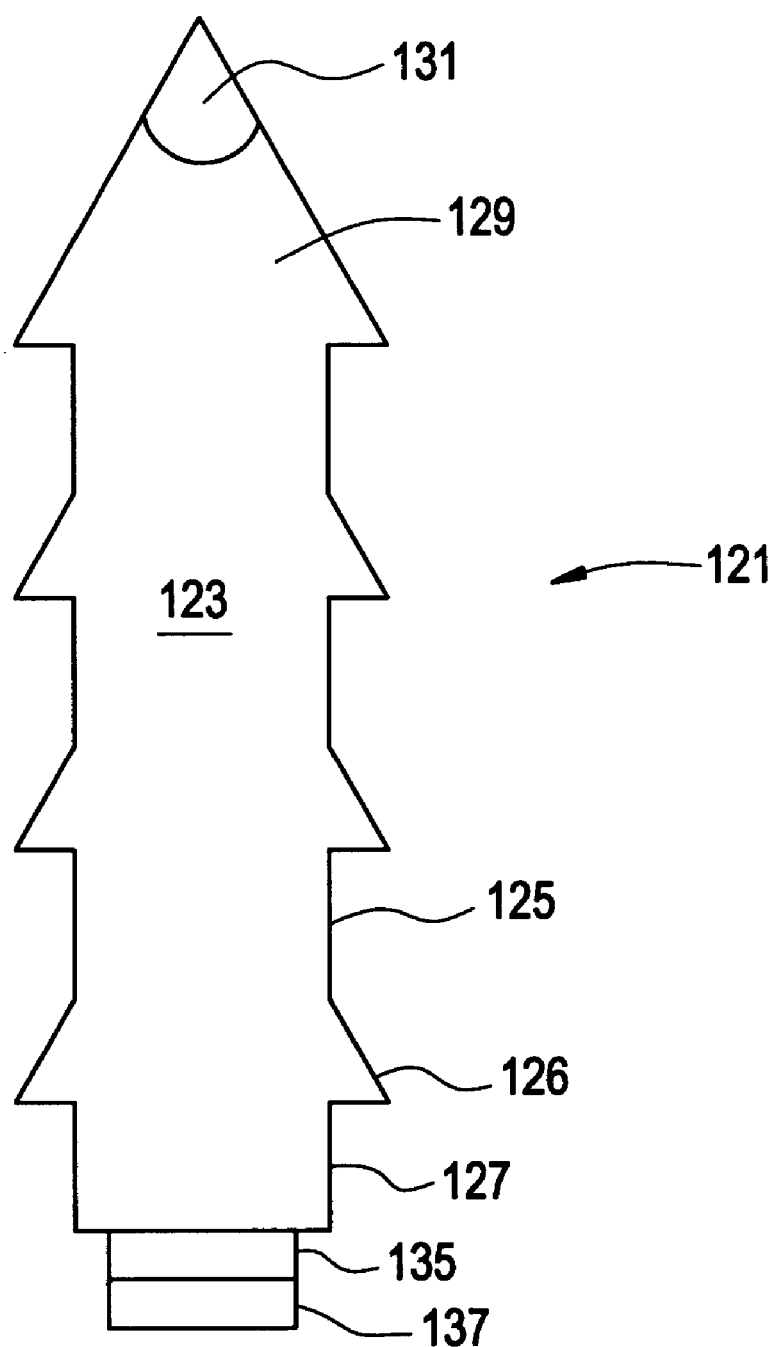
FIG. 15 represents a cross-section of an implant of the present invention having a red light LED and an Rf antenna.

In some embodiments, a bone screw is provided with the red light LED. Now referring to FIG. 15, in some embodiments, the bone screw 121 comprises:
a) a body portion 123 made from a light transmissible material (such as single crystal sapphire),
b) an outer surface 125 at least a portion of which is threaded 126,
c) a proximal portion 127,
d) a distal portion 129 containing a reflective head portion 131 having a convex reflective surface,
e) a red light source 135 (such as an LED) disposed upon the proximal portion of the screw, and
f) an antenna 137 in electrical connection with the light source.

In other embodiments, the red light LED and antenna are replaced with a light port, and the light source is externally based.

The present inventors believe that AD may be more effectively prevented than treated. Prevention is more likely to be the most-cost effective approach, considering the enormous cost and morbidity of AD-related complications. It would be desirable to achieve a low inflammatory, low oxidant environment in the brain. This could be accomplished by regulating diet for high risk AD patients.

We claim:

1. A method of treating a patient having an olfactory bulb, comprising:
   a) inserting a red light probe having a red light emitter into an upper portion of a nasal cavity,
   b) orienting the red light emitter towards the cribriform plate, and
   c) activating the emitter to irradiate the olfactory bulb with an effective amount of red light.

2. The method of claim 1 wherein the red light provides treatment to a damaged olfactory bulb.

3. The method of claim 1 wherein the red light provides preventative treatment to an undamaged olfactory bulb.

4. The method of claim 1 wherein the red light is provided through a cribriform plate.

5. The method of claim 1 wherein the red light irradiates the olfactory cortex.

6. The method of claim 1 wherein the red light is provided in a dose of 0.02 J/cm$^2$ to about 200 J/cm$^2$.

7. The method of claim 1 wherein the red light is provided in a wavelength of between 600 nm and 1000 nm.

8. The method of claim 1 wherein the red light is provided in a wavelength of between 600 nm and 700 nm.

9. The method of claim 1 wherein the red light is provided in a wavelength of between 800 nm and 900 nm.

10. The method of claim 1 wherein the red light is provided on about a daily basis.

11. The method of claim 1 wherein the red light is provided for the purpose of improving learning or memory in an undamaged brain.

* * * * *